(12) United States Patent
Kato et al.

(10) Patent No.: US 10,500,387 B2
(45) Date of Patent: Dec. 10, 2019

(54) MICRONEEDLE UNIT (71) Applicant: TOPPAN PRINTING CO., LTD., Taito-ku (JP)

(72) Inventors: Hiroyuki Kato, Taito-ku (JP); Hisami Ueno, Taito-ku (JP)

(73) Assignee: TOPPAN PRINTING CO., LTD., Taito-ku (JP)

(*) Notice: Subject to any disclaimer, the term of this patent is extended or adjusted under 35 U.S.C. 154(b) by 0 days.

(21) Appl. No.: 15/376,889

(22) Filed: Dec. 13, 2016

(65) Prior Publication Data

US 2017/0087346 A1 Mar. 30, 2017

Related U.S. Application Data (63) Continuation of application No. PCT/JP2015/062515, filed on Apr. 24, 2015.

(30) Foreign Application Priority Data

Jun. 18, 2014 (JP) ................................. 2014-125400

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01);
(Continued)

(58) Field of Classification Search
CPC .............. A61M 37/0015; A61M 37/00; A61M 2037/003; A61M 2037/0023;
(Continued)

(56) References Cited

U.S. PATENT DOCUMENTS

| 4,505,891 A | 3/1985 | Ito | |
|---|---|---|---|
| 2006/0127463 A1* | 6/2006 | Nugara | A61K 9/703 424/448 |

(Continued)

FOREIGN PATENT DOCUMENTS

| EP | 3 097 942 A1 | 11/2016 |
|---|---|---|
| JP | 57-77617 A | 5/1982 |

(Continued)

OTHER PUBLICATIONS

Extended Search Report dated May 12, 2017 in European Patent Application No. 15809752.7.

(Continued)

*Primary Examiner* — Amber R Stiles
(74) *Attorney, Agent, or Firm* — Oblon, McClelland, Maier & Neustadt, L.L.P.

(57) ABSTRACT

A microneedle unit including a microneedle having a first surface and a second surface opposite to the first surface, the microneedle being flexible and having one or more projections on the first surface, and a support member connected to the second surface of the microneedle such that the support member supports the microneedle. The support member includes an adhesive portion and a rigid portion connected to the adhesive portion, the adhesive portion is adhesive to skin and extends outside of the second surface in plan view of the second surface, and the rigid portion includes a rigid plate which is more rigid than the adhesive portion and the microneedle.

20 Claims, 7 Drawing Sheets (52) U.S. Cl.
CPC ............ *A61M 2037/0046* (2013.01); *A61M 2037/0053* (2013.01)

(58) Field of Classification Search
CPC .. A61M 2037/0046; A61M 2037/0053; A61M 2025/0093; A61K 9/0021; A61K 9/7084; A61F 2013/00906
See application file for complete search history.

(56) References Cited

U.S. PATENT DOCUMENTS

| | | | |
|---|---|---|---|
| 2009/0182306 A1* | 7/2009 | Lee ..................... | A61K 9/0021 604/506 |
| 2010/0256568 A1* | 10/2010 | Frederickson .... | A61M 37/0015 604/173 |
| 2015/0305739 A1* | 10/2015 | Rolandi ................ | A61B 17/08 606/221 |
| 2016/0325081 A1 | 11/2016 | Kato | |

FOREIGN PATENT DOCUMENTS

| | | |
|---|---|---|
| JP | 2006-345984 A | 12/2006 |
| JP | 2008-543528 A | 12/2008 |
| JP | 2010-022780 A | 2/2010 |
| JP | 2010-063666 A | 3/2010 |
| JP | 2013-112671 A | 6/2013 |
| WO | WO 2007/002522 A1 | 1/2007 |
| WO | WO 2008/020632 A1 | 2/2008 |

OTHER PUBLICATIONS

International Search Report dated Jun. 30, 2015 in PCT/JP2015/062515, filed Apr. 24, 2015.
Office Action dated Jun. 4, 2019 in corresponding Japanese Patent Application No. 2016-529146 (with English-language Translation), 2 pages.

\* cited by examiner

MICRONEEDLE UNIT

CROSS-REFERENCE TO RELATED APPLICATIONS

The present application is a continuation of International Application No. PCT/JP2015/062515, filed Apr. 24, 2015, which is based upon and claims the benefits of priority to Japanese Application No. 2014-125400, filed Jun. 18, 2014. The entire contents of these applications are incorporated herein by reference.

BACKGROUND OF THE INVENTION

Field of the Invention

The present invention relates to microneedle units having microneedles.

Discussion of the Background

Transdermal absorption is a method of administering a substance into the body by infiltrating the substance such as a drug into the body through the skin. Transdermal absorption is also a convenient method of administering a substance into the body without causing pain to an administration target such as a human.

In the transdermal absorption method, it has been proposed to administer drugs into the skin by piercing a microneedle into the skin. The microneedle includes a projection with a size that does not provoke pain in the administration target. The projection is configured to penetrate through the stratum corneum, which is a barrier layer of the skin. As the drug is absorbed into the skin through a hole created in the skin by the microneedle, the drug is percutaneously absorbed (for example, see PTL 1).

PTL 1: WO 2008/020632

SUMMARY OF THE INVENTION

According to one aspect of the present invention, a microneedle unit includes a microneedle having a first surface and a second surface opposite to the first surface, the microneedle being flexible and having one or more projections on the first surface, and a support member connected to the second surface of the microneedle such that the support member supports the microneedle. The support member includes an adhesive portion and a rigid portion connected to the adhesive portion, the adhesive portion is adhesive to skin and extends outside of the second surface in plan view of the second surface, and the rigid portion includes a rigid plate which is more rigid than the adhesive portion and the microneedle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

With reference to FIGS. 1 to 7, a microneedle unit according to an embodiment of the present invention will be described. A configuration of a microneedle unit, a configuration of a rigid plate, a configuration of a microneedle, a forming material of the microneedle, a manufacturing method for a microneedle and operation of the microneedle unit will be individually described in each of the sections below.

Configuration of Microneedle Unit

Figure 1:
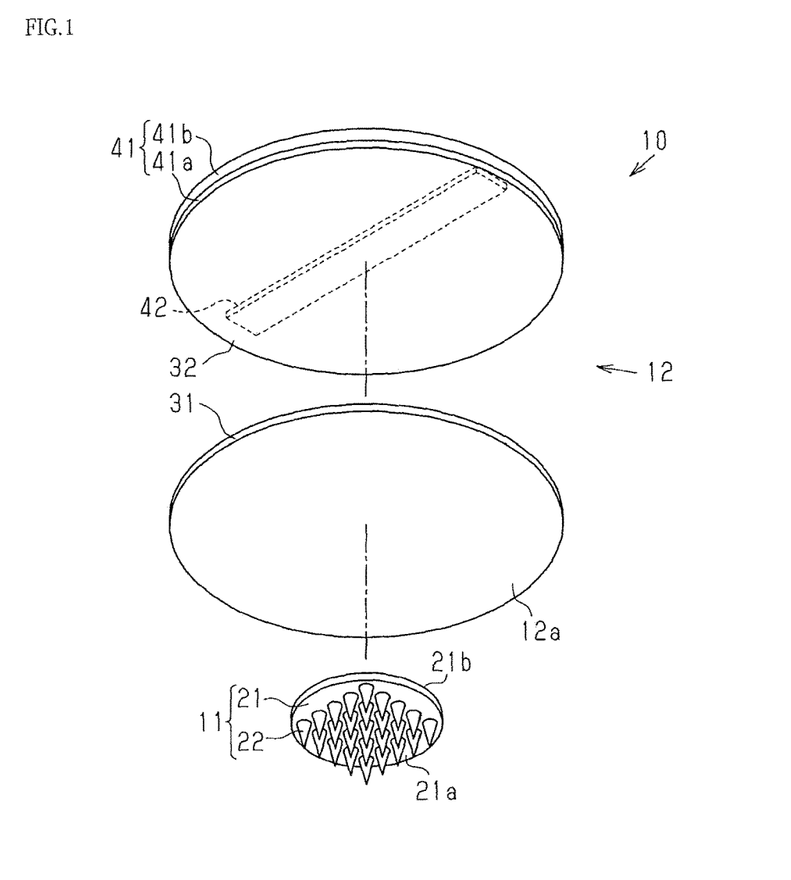
FIG. 1 is an exploded perspective view of a microneedle unit according to the first embodiment of the present invention.

With reference to FIG. 1, a configuration of a microneedle unit will be described.

As shown in FIG. 1, a microneedle unit 10 includes a microneedle 11 and a support section 12 that supports the microneedle 11. The microneedle 11 includes a substrate 21 and at least one projection 22. The substrate 21 is made up of a plurality of surfaces, of which a surface having the projection 22 is a projection forming surface 21a, and a surface opposite from the projection forming surface 21a is a supported surface 21b. The projection forming surface 21a is an example of the first surface, and the supported surface 21b is an example of the second surface.

The substrate 21 of the microneedle 11 has, for example, a disc shape. The substrate 21 may not necessarily have a disc shape and may have a polygonal plate shape such as a rectangular plate shape. The projection forming surface 21a of the substrate 21 may have an area not smaller than an area that can be provided with at least one projection 22. Further, the projection forming surface 21a of the substrate 21 may have a flat surface, curved surface, or may have both a flat surface and a curved surface. The supported surface 21b of the substrate 21 may have a flat surface, a curved surface, or may have both a flat surface and a curved surface.

On the projection forming surface 21a of the substrate 21, a plurality of projections 22 are regularly disposed in a center area of the projection forming surface 21a, for example, at junctions of grid. The plurality of projections 22 may be disposed in any area other than the center area of the projection forming surface 21a of the substrate 21, or alternatively, may be irregularly arranged or regularly arranged in any pattern on the projection forming surface 21a. For example, when the plurality of projections 22 are regularly arranged, the plurality of projections 22 may be arranged in a close-packed pattern or a concentric pattern.

Each projection 22 has, for example, a conical shape that extends in a direction, which is an extending direction. Further, the projection 22 may have a polygonal pyramid shape, which is a pyramid shape other than a conical shape. Alternatively, the projection 22 may have a frustum shape including a conical frustum and a pyramidal frustum, a columnar shape including a cylinder and a polygonal prism, or a blade shape.

Further, the projection 22 may have two or more different shapes in the extending direction, for example, two or more of the pyramid shape, frustum shape, columnar shape, and blade shape. An outer peripheral surface of the projection 22 may have a twist or a step. For facilitating puncture of the projection 22 into the skin, at least a tip of the projection 22 preferably has a pyramid shape.

Although the plurality of projections 22 have the same shape, they may have different shapes from each other. For the purpose of facilitating manufacturing of the plurality of projections 22, it is preferable that the plurality of projections 22 have an identical shape. Although the plurality of projections 22 extend in the same direction, they may extend in directions crossing each other. When the plurality of projections 22 extend in directions crossing each other, the extending directions of the projections 22 are preferably such that the tip of the projection 22 is not in contact with the tip of another projection 22 and the tips of the plurality of projections 22 are preferably located on the same plane. Although the plurality of projections 22 have the same length in the extending direction, they may have different lengths from each other in the extending direction.

The support section 12 has, for example, a disc shape, and is made up of a plurality of surfaces, of which a surface bonded to the supported surface 21b of the microneedle 11 is a bonding surface 12a. The bonding surface 12a of the support section 12 is in contact with the supported surface 21b of the microneedle 11, thereby supporting the microneedle 11. The support section 12 is not limited to a disc shape, and may be, for example, a polygonal disc shape.

The bonding surface 12a of the support section 12 has an area larger than the area of the supported surface 21b of the substrate 21 such that the bonding surface 12a extends outward from the supported surface 21b of the substrate 21 in plan view of the supported surface 21b. Further, the bonding surface 12a of the support section 12 may have a flat surface, curved surface, or may have both a flat surface and a curved surface. For example, when the supported surface 21b of the substrate 21 has a protruding shape which protrudes toward the support section 12, the bonding surface 12a of the support section 12 preferably has a recessed shape which is recessed in a direction away from the microneedle 11.

The support section 12 includes an adhesive layer 31 and a rigid section 32. The adhesive layer 31 constitutes the bonding surface 12a that is in contact with the supported surface 21b of the microneedle 11 so as to adhere the microneedle 11 to the support section 12, and extends outward from the supported surface 21b of the microneedle 11 in plan view of the supported surface 21b. Further, the adhesive layer 31 has adhesiveness to the skin of a puncture target of the microneedle 11 such that the adhesive layer 31 remains adhered to the skin after the force for piercing the microneedle 11 into the skin is released. A forming material of the adhesive layer 31 is, for example, an acrylic acid adhesive. The adhesive layer 31 is an example of the adhesive section.

The support section 12 includes the adhesive layer 31 on a surface that faces the puncture target of the microneedle 11. Accordingly, when the microneedle 11 is pierced into the skin, the adhesive layer 31 along with the microneedle 11 is pressed against the skin. Accordingly, the microneedle unit 10 is adhered to the skin by the adhesiveness of the adhesive layer 31.

The rigid section 32 has flexibility to bend along with the projection forming surface 21a of the microneedle 11 when subject to an external force that bends the projection forming surface 21a of the microneedle 11. Further, the rigid section 32 includes a rigid plate 42 having rigidity higher than rigidity of the microneedle 11 and the adhesive layer 31.

The rigid section 32 includes the rigid plate 42 and a base layer 41 that sandwiches the rigid plate 42. The base layer 41 is made up of a support layer 41a that supports the rigid plate 42 and a cover layer 41b that covers the rigid plate 42, and the rigid plate 42 is sandwiched between the support layer 41a and the cover layer 41b. A forming material of the support layer 41a may be any material that allows the adhesive layer 31 to be adhered to the support layer 41a and can support the rigid plate 42. The base layer 41 has rigidity lower than rigidity of the rigid plate 42.

The forming material of the support layer 41a is polyethylene, polyurethane or the like. Of these materials, polyurethane is preferable since it has a texture preferable for use by a human, for example, is easily fitted to the skin when the puncture target of the microneedle 11 is a human. A forming material of the cover layer 41b may be any material that can support the rigid plate 42, similarly to the support layer 41a. The forming material of the cover layer 41b is polyethylene, polyurethane or the like. Of these materials, polyurethane is preferable for the same reason described above.

Although the forming material of the support layer 41a and the forming material of the cover layer 41b may be the same or different from each other, the same forming material is preferably used for the support layer 41a and the cover layer 41b. Accordingly, when the support layer 41a and the cover layer 41b are bonded to each other with the rigid plate 42 sandwiched therebetween, the adhesiveness between the support layer 41a and the cover layer 41b is enhanced compared with the case where the forming material of the support layer 41a and the forming material of the cover layer 41b are different from each other. Further, the number of types of forming materials for the microneedle unit 10 can be reduced. Moreover, when the support section 12 has a disc shape, the support layer 41a and the cover layer 41b can be in the same shape. In this case, the forming material for the support layer 41a and the forming material for the cover layer 41b do not need to be separately prepared.

Of the surfaces of the cover layer 41b, a surface which constitutes a surface of the support section 12 and does not face at least the rigid plate 42 is preferably in a pale orange tone. In this configuration, the difference between the color of skin and the color of the microneedle unit 10 placed on the skin can be reduced when the punctuation target of the microneedle 11 is a human. Accordingly, the contrast between the microneedle unit 10 and the skin can be reduced.

Of the surfaces of the cover layer 41b, a surface which does not face at least the rigid plate 42 has preferably a mat finish. The mat finish is a so-called pear skin finish applied on the surface of the cover layer 41b, which reduces reflection of light on the surface of the cover layer 41b. Accordingly, the contrast between the microneedle unit 10 and the skin can be reduced.

In order to bond the support layer 41a to the cover layer 41b to each other with the rigid plate 42 sandwiched therebetween, an adhesive is applied on the support layer 41a and the cover layer 41b. The adhesive is not limited as long as it can adhere the support layer 41a and the cover layer 41b and, for example, may be a vinyl acetate adhesive, acrylic acid adhesive or the like.

Configuration of Rigid Plate

Figure 2:
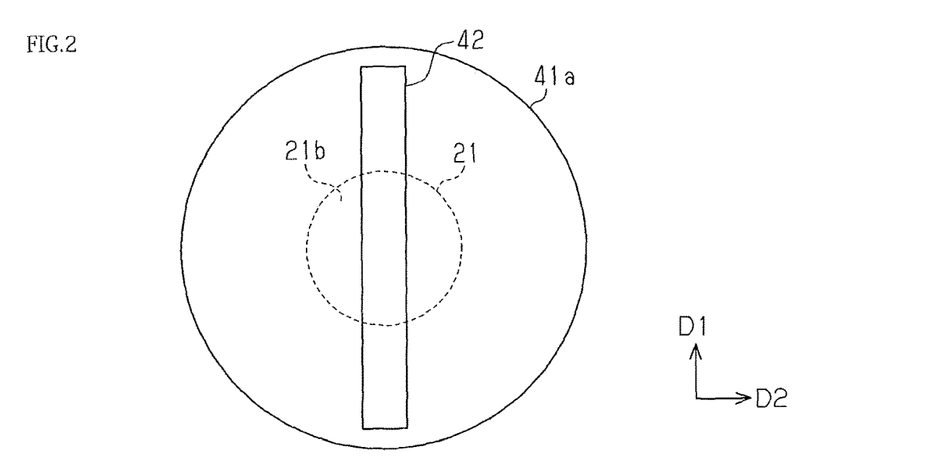
FIG. 2 is a plan view which shows a plan configuration of a rigid plate and a support layer.

With reference to FIG. 2, a configuration of the rigid section included in the support section will be described. For convenience of explanation of a shape of the rigid plate 42, the cover layer 41b of the base layer 41 is not shown in FIG. 2.

As shown in FIG. 2, the rigid plate 42 has, for example, a plate shape that extends in a direction, which is a first direction D1. A center part of the rigid plate 42 in the first direction D1 overlaps a center part of the microneedle 11 in a radial direction in plan view of the supported surface 21b of the microneedle 11. A width of the rigid plate 42 in the first direction D1 is larger than a diameter of the microneedle 11, and the width of the rigid plate 42 in the second direction D2 is smaller than the diameter of the microneedle 11.

The rigid section 42 has flexibility to bend along with the projection forming surface 21a of the microneedle 11 when subject to an external force that bends the projection forming surface 21a of the microneedle 11, and rigidity higher than rigidity of the adhesive layer 31 and the microneedle 11. Since the rigid plate 42 has rigidity higher than rigidity of the adhesive layer 31 and the microneedle 11, the rigid section 32 which includes the rigid plate 42 has rigidity higher than rigidity of the adhesive layer 31 and the microneedle 11. The rigidity of the rigid plate 42 is of such an extent that the rigid plate 42 remains deformed after the external force that bends the projection forming surface 21a is released.

The support section 12 is deformed, for example, along the bone of a user when the support section 12 is pressed against the skin by a user. For example, when the microneedle unit 10 is pressed against the skin surface having a protruding shape which protrudes toward the microneedle unit 10, the microneedle unit 10 is deformed into a recessed shape so that the microneedle 11 is located on the top of the protruding shape. Accordingly, the rigid plate 42 is deformed so that the projection forming surface 21a of the microneedle 11 conforms to the skin surface.

On the other hand, when the microneedle unit 10 is pressed against the skin surface having a recessed shape which is recessed in a direction away from the microneedle unit 10, the microneedle unit 10 is deformed into a protruding shape so that the microneedle 11 is located on the bottom of the protruding shape. Accordingly, the rigid plate 42 is deformed so that the projection forming surface 21a of the microneedle 11 conforms to the skin surface.

Moreover, when the microneedle unit 10 is pressed against the skin surface having a flat shape, the rigid plate 42 is deformed so that the projection forming surface 21a of the microneedle 11 conforms to the shape of the skin surface.

When the microneedle 11 is pierced into the skin such as of the arm or face, a portion of the skin against which the microneedle 11 is pressed is stretched by a user so that the microneedle 11 is pressed against the stretched skin surface. When the microneedle 11 is pierced into the skin, the rigid plate 42 is deformed along the shape of the skin surface so that the projection forming surface 21a of the microneedle 11 conforms to the skin surface as described above. Accordingly, the adhesive layer 31 is adhered to the skin surface with the rigid plate 42 deformed.

Then, a user releases a force of pressing the microneedle 11 and a force of stretching the skin. As the force is released, the skin contracts to return to the original shape from the stretched state. Accordingly, in the support section 12, a restoring force of the skin is applied from the skin surface to the adhesive layer 31 adhered to the skin surface while the rigidity of the rigid plate 42 acts on the adhesive layer 31 via the rigid section 32 bonded to the adhesive layer 31 so as to reduce deformation of the adhesive layer 31. That is, the rigid plate 42 exerts a reaction force against the restoring force of the skin onto the skin via the adhesive layer 31. As a result, as the support section 12 exerts a force onto to the skin in a direction opposite from a direction in which the skin contracts (restoring direction), contraction (restoration) of the skin is reduced or the speed of contraction (restoring speed) of the skin is lowered.

In particular, when an extending direction of the rigid plate 42 is parallel to the stretched direction of the skin, the rigid plate 42 has a maximum effect of preventing deformation of the skin. On the other hand, when the extending direction of the rigid plate 42 intersects the stretched direction of the skin, the rigid plate 42 also prevents deformation of the skin to a certain extent. In addition, when the extending direction of the rigid plate 42 intersects the stretched direction of the skin, deformation of the skin is reduced at least in a portion where the microneedle 11 overlaps the rigid plate 42 in plan view of the supported surface 21b of the microneedle 11.

The forming material for the rigid plate 42 is, for example, a resin, and is preferably a polyester such as polyethylene terephthalate or polylactic acid, or a high elastic modulus thermoplastic resin such as acrylic resin or polyamide resin. Alternatively, the forming material for the rigid plate 42 may be a thermosetting polymer such as acrylic resin, polyester, and epoxy resin. According to the rigid plate 42 made of a resin, the rigid plate 42 has a rigidity suitable for use on the human skin, in particular, the skin of the face or arm. Accordingly, the rigid plate 42 made of a resin can prevent detachment of the microneedle from the skin by suppressing deformation of the skin, and reduce a feeling of tightness of the skin on the puncture target of the microneedle by suppressing deformation of the skin.

Alternatively, the rigid plate 42 may also be implemented by a metal strip. The metal strip is preferable in that it has an improved ability of maintaining the shape of the microneedle 11 compared with the rigid plate 42 made of a resin.

Configuration of Microneedle

Figure 3:
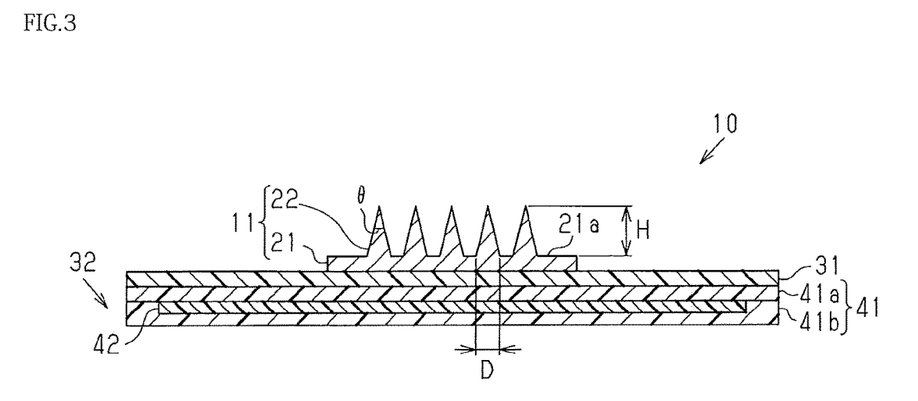
FIG. 3 is a sectional view which shows a cross sectional configuration of the microneedle unit.

With reference to FIG. 3, a configuration of a microneedle 11 will be described. FIG. 3 shows a plane extending in the first direction of FIG. 2, as viewed in a cross section taken along a plane passing through the base layer 41, the rigid plate 42, the adhesive layer 31, and the microneedle 11.

As shown in FIG. 3, in the projection 22 of the microneedle 11, a height H of the projection 22 is a length in the extending direction from the projection forming surface 21a of the substrate 21 to the tip of the projection 22 which is a distal end away from the substrate 21. The projection 22 preferably has the height H suitable for creating a hole in the skin, and the height H of the projection 22 is preferably in the range from 10 μm to 1000 μm.

The height H of the projection 22 is preferably designed depending on where in the skin that the bottom of the hole to be formed in the target should be located. When the bottom of the hole is designed to be located in the stratum corneum, the height H of the projection 22 is preferably in the range from 10 μm to 300 μm, more preferably in the range from 30 μm to 200 μm.

When the bottom of the hole is designed to pass through the stratum corneum of the skin and to be located at a position not reaching the nerve plexus, the height H of the projection 22 is preferably in the range from 200 μm to 700 μm, more preferably in the range from 200 μm to 500 μm. When the bottom of the hole is designed to pass through the stratum corneum of the skin and to be located at a position not reaching the nerve plexus, the height H of the projection 22 is further preferably in the range from 200 μm to 300 μm.

When the bottom of the hole is designed to be located at a position reaching the dermis, the height H of the projection 22 is preferably in the range from 200 μm to 500 μm. When the bottom of the hole is designed to be located at a position reaching the epidermis, the height H of the projection 22 is preferably in the range from 200 μm to 300 μm.

In the projection 22, the maximum length in the direction perpendicular to the extending direction is a width D, and the width D of the projection 22 is preferably in the range from 1 μm to 300 μm. For example, when the projection 22 has a regular quadrangular pyramid shape or a square column shape, the proximal end which is different from the distal end of the projection 22 defines a square shape on the projection forming surface 21a. The length of the diagonal line of the square area defined by the proximal end of the projection 22 corresponds to the width D of the projection 22. Further, for example, when the projection 22 has a conical shape or a columnar shape, the proximal end of the projection 22 defines a circular area on the projection forming surface 21a. The diameter of the circular shape defined by the proximal end of the projection 22 corresponds to the width D of the projection 22.

In the projection 22, an aspect ratio A is the ratio of the height H to the width D (A=H/D). The aspect ratio A of the projection 22 is preferably in the range from 1 to 10.

When the projection 22 has a pyramid shape at least on the distal end, the angle of the distal end of the projection 22 is a distal end angle θ. The distal end angle θ is a maximum angle of the projection 22 in the cross section taken along the plane perpendicular to the bonding surface 12a of the substrate 21. For example, when the projection 22 has a regular quadrangular pyramid shape, the distal end angle θ of the projection 22 corresponds to an apex angle of an isosceles triangle having the proximal end of the projection 22 as a base and the distal end of the projection 22 as an apex.

When the projection 22 has a pyramid shape at least on the distal end and the bottom of the hole is designed to be located at a position that passes through the stratum corneum, the distal end angle θ is preferably in the range from 5 degrees to 30 degrees, more preferably in the range from 10 degrees to 20 degrees.

Forming Material for Microneedle

The forming material of the microneedle 11 is preferably a biocompatible material, that is, a material which functions as the microneedle 11 but does not adversely affect the target to which the microneedle 11 is applied. When the forming material of the microneedle 11 is a biocompatible material, the forming material is silicon, metal, resin or the like. When the forming material of the microneedle 11 is a metal, the forming material is stainless steel, titanium, manganese or the like. When the forming material of the microneedle 11 is a resin, the forming material is medical grade silicone, polylactic acid, polyglycolic acid, polycarbonate cyclic olefin copolymer or the like.

The forming material of the microneedle 11 may be a material having biocompatibility and dissolved in liquid. When the forming material is a material which is dissolved in liquid, the forming material is, for example, a water soluble polymer. The water soluble polymer is, for example, alginates, curdlan, chitin, chitosan, glucomannan, polymalic acid, collagen, collagen peptide, hydroxypropyl cellulose, hydroxypropylmethyl cellulose, carboxymethyl cellulose, gelatin, chitosan succinamide, trimethyl chitosan, oligo chitosan, oligo chitin, ethylene glycol chitosan, ethylene glycol chitin or the like.

In the microneedle unit according to the present embodiment, the forming material for the microneedle 11 is not limited to the specific materials described above.

In the microneedle 11, the forming material of the substrate 21 and the forming material of the projection 22 may be the same or different from each other. In the plurality of projections 22 of the microneedle 11, the forming material of the plurality of projections 22 may be the same or different from each other.

In the microneedle unit according to the present embodiment, the forming material of the substrate 21 and the forming material of the projection 22 of the microneedle 11 preferably contain a water soluble polymer. The microneedle 11 having the substrate 21 and the projection 22 made of a water soluble polymer has high softness. Accordingly, an effect of the present embodiment can be enhanced.

Further, when the forming material of the microneedle 11 is a material dissolved in liquid, the microneedle 11 may include a drug administered into the skin as a forming material. The drug administered into the skin is pharmacologically active agents, cosmetic composition or the like. When the drug is a pharmacologically active agent, the drug is appropriately selected depending on the user's application. When the drug is a pharmacologically active agent, the drug is, for example, vaccines such as influenza vaccine, pain relievers for cancer patients, insulin, biologics, gene therapy agents, injections, oral agents, skin application preparations or the like.

Since the microneedle 11 is pierced into the skin, transdermal administration using the microneedle unit 10 is also applied to pharmacologically active agents that need to be subcutaneously injected, besides the pharmacologically active agents which are conventionally used for transdermal administration. Particularly, when an injection agent such as vaccine is administered, transdermal administration using the microneedle unit 10 does not cause pain during drug administration.

Accordingly, transdermal administration using the microneedle unit 10 is preferably applied to children. Further, in transdermal administration using the microneedle unit 10, a patient does not need to take the drug orally during drug administration. Accordingly, the microneedle unit 10 is preferably applied to children who have difficulty in taking oral medication.

A cosmetic composition is a composition for use as cosmetics and beauty products. When the drug is a cosmetic composition, the drug is, for example, humectants, colorants, fragrance, physiologically active agents exhibiting cosmetic effects. Active agents exhibiting cosmetic effects are, for example, substances having improvement effects on wrinkles, acne, stretch marks and the like, or substance having improvement on hair loss.

Method for Manufacturing Microneedle

A method for manufacturing the microneedle 11 may be one of a variety of known methods. When the forming material of the microneedle 11 is a resin, a method for manufacturing the microneedle 11 may be one of the injection molding method, extrusion molding method, imprint method, hot embossing method, casting method and the like.

When the forming material of the microneedle 11 is silicon or metal, a method for manufacturing the microneedle 11 may be one of the machining method such as cutting, etching method and the like.

Regardless of whether the forming material of the microneedle 11 is any of the above materials, a method for manufacturing the microneedle 11 may be a reproducing method using an intaglio plate as an original plate of the microneedle 11. The intaglio plate is manufactured by, for example, a plating method or a molding method using a resin.

Operation of Microneedle Unit

With reference to FIGS. 4 to 7, an operation of the microneedle unit 10 when the user pierces the microneedle 11 into the skin of the puncture target of the microneedle 11 will be described. The skin of the puncture target of the microneedle 11 may be, for example, the skin of humans or skin of animals other than humans. The following describes an example where the microneedle 11 is pierced into the skin, having a protruding shape which protrudes toward the microneedle 11 and the extending direction of the rigid plate 42 substantially coincides with the stretched direction of the skin.

Figure 4:
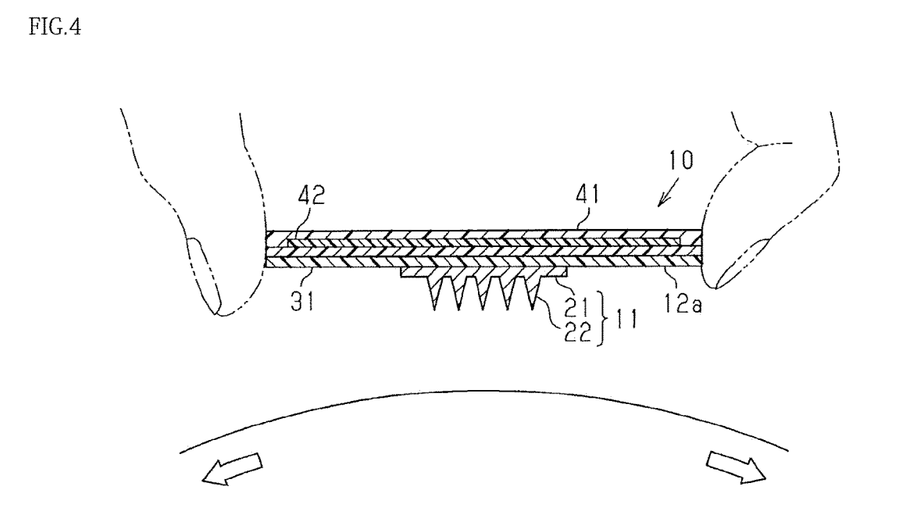
FIG. 4 is an operation view which shows operation of the microneedle unit.

As shown in FIG. 4, when the user pierces the microneedle unit 10 into the skin, the user stretches a portion of the skin where the projections 22 of the microneedle 11 are pierced by using one hand, for example, the thumb and index finger of the left hand. Then, the user holds the microneedle unit 10 by the other hand, for example, the thumb and index finger of the right hand, and brings the microneedle unit 10 close to the portion of the skin stretched by the left hand.

Figure 5:
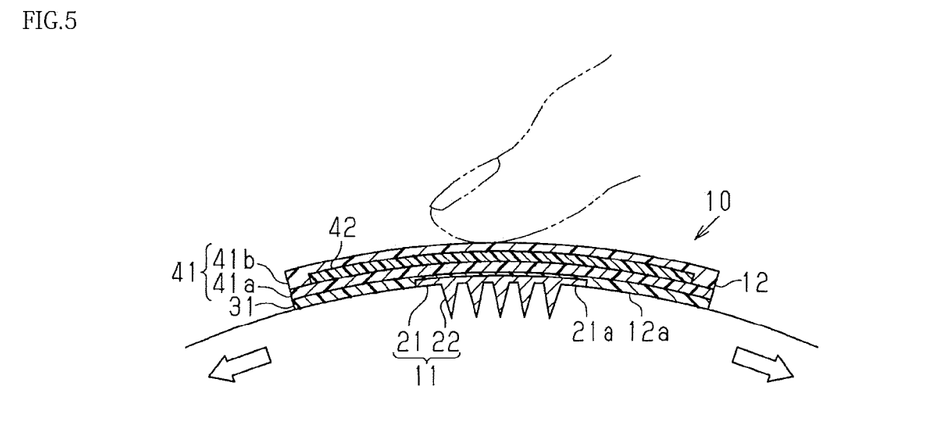
FIG. 5 is an operation view which shows operation of the microneedle unit.

As shown in FIG. 5, the user puts the microneedle unit 10 on the skin, and presses the support section 12 of the microneedle unit 10 against the stretched skin. Accordingly, the projections 22 of the microneedle 11 are pierced into the skin. In this state, the adhesive layer 31 and the rigid plate 42 curve with the bonding surface 12a facing the skin so that the projection forming surface 21a of the microneedle 11 conforms to the skin surface. Further, as the adhesive layer 31 is pressed against the skin, the adhesive layer 31 extends on and around the substrate 21 of the microneedle 11. Accordingly, the adhesive layer 31 causes the microneedle 11, and the rigid plate 42 and the base layer 41 located on the adhesive layer 31, to be deformed extending along the shape of the skin surface and adhered to the skin.

Figure 6:
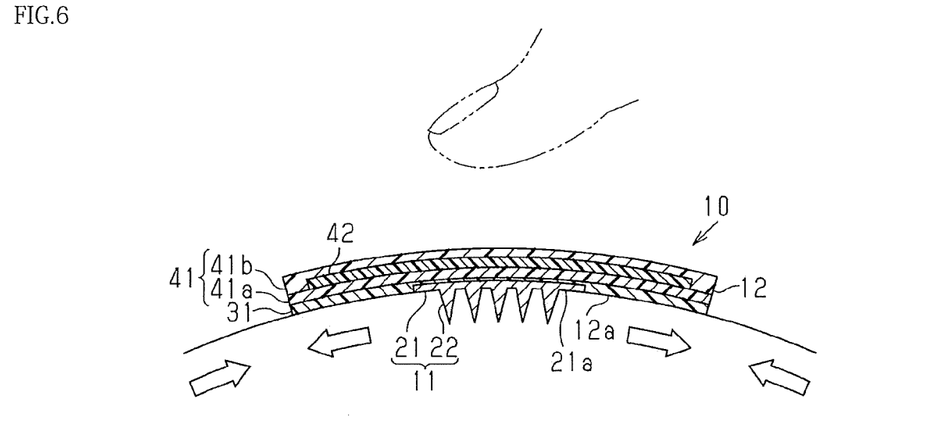
FIG. 6 is an operation view which shows operation of the microneedle unit.

As shown in FIG. 6, after the projections 22 of the microneedle 11 are pierced into the skin, the user releases the force stretching the skin and the force pressing the microneedle unit 10 against the skin. Accordingly, the skin starts to contract in the direction opposite to the stretched direction so as to return to the original shape.

However, the rigid plate 42 of the microneedle unit 10 exerts a reaction force due to the rigidity of the rigid plate 42 against the adhesive layer 31 which is subject to a deformation force in the direction in which the skin contracts, and thus exerts a reaction force against the skin surface via the adhesive layer 31. Accordingly, the rigid plate 42 of the microneedle 11 acts a force on the skin in the direction opposite to the contract direction of the skin. As a result, deformation of the skin is prevented, or the speed of deformation of the skin is lowered.

Figure 7:
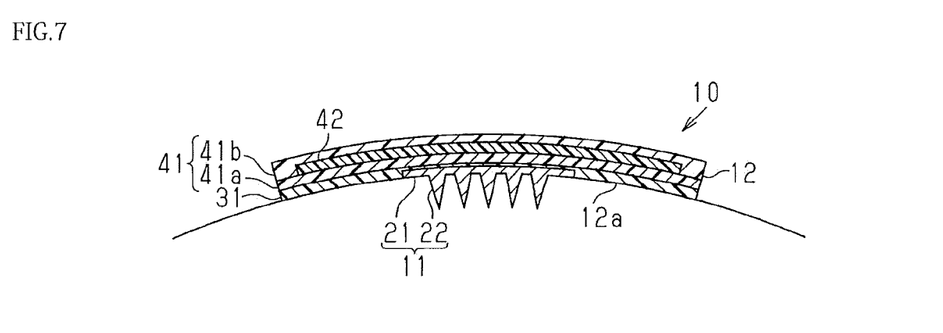
FIG. 7 is an operation view which shows operation of the microneedle unit.

As shown in FIG. 7, the projections 22 of the microneedle 11 pierced into the skin turns to be not easily detached from the skin. This prevents the microneedle 11 from being detached from the skin after the force that presses the microneedle 11 against the skin is released.

The microneedle unit 10 may not be necessarily attached to the skin by using both hands. For example, stretching a portion of the skin where the microneedle 11 is pierced, and pressing the microneedle unit 10 against the skin can be done by one hand at the same time. In this case as well, the effect which is the same as the above can be achieved by the microneedle unit 10. Further, in the case where the microneedle 11 is pierced into the skin surface having a recessed shape or a flat shape as described above, the effect which is the same as the above can also be achieved.

Example

Step of Manufacturing Microneedle

In manufacturing of the microneedle 11, an original plate of the microneedle 11 was fabricated by micromachining of a silicon substrate. The silicon substrate was provided with a disc shaped substrate and 36 projections, each formed in a regular quadrangular pyramid shape with a height H of 150 μm and a base side length of 60 μm. The respective 36 projections were disposed with an interval of 1 mm in a matrix of 6 columns and 6 lines.

Then, the original plate of the microneedle 11 formed of a silicon substrate was plated with nickel to form a nickel film with a thickness of 500 μm. After the nickel film was formed, the original plate was etched by wet etching by using 30 wt % potassium hydroxide aqueous solution heated to 90° C. to form an intaglio plate made of nickel.

After the intaglio plate was fabricated, hydroxypropyl cellulose in the liquid form was supplied to the intaglio plate. Then, hydroxypropyl cellulose was cured by heat from a heat source. The cured hydroxypropyl cellulose was peeled off from the intaglio plate to obtain the microneedle 11 having the substrate 21 and the plurality of projections 22.

Step of Manufacturing Support Section

In manufacturing of the support section 12, two urethane sheets were provided as the base layer 41 that covers the rigid plate 42, and a plate member made of polyester was provided as a plate member that constitutes the rigid plate 42. The two urethane sheets had the disc shape with the same size. The polyester plate member was a rectangular plate extending in one direction.

An acrylic acid adhesive was applied on both surfaces of one of the urethane sheet and on one surface of the polyester plate member. One surface of one of the urethane sheets was bonded to a surface of the polyester plate member on which the acrylic acid adhesive was applied. Accordingly, the adhesive layer was formed as a layer of the acrylic acid adhesive which was applied on a surface of the urethane sheet with which the polyester plate member was not in contact.

Then, the acrylic acid adhesive was applied on one surface of the other urethane sheet, and the urethane sheet was placed to cover the polyester plate member while the surface of the urethane sheet on which the acrylic acid adhesive was applied was oriented to the polyester plate member. Then, the two urethane sheets were bonded together with the polyester plate member sandwiched between the two urethane sheets to thereby form the support section 12.

Step of Manufacturing Microneedle Unit

The supported surface 21b of the microneedle 11 was bonded to the adhesive layer 31 that constituted the bonding surface 12a of the support section 12 to thereby form the microneedle unit 10.

Comparison Example

As a Comparison example, a microneedle unit which did not include the polyester plate member (rigid plate 42) was manufactured by the method described below.

Step of Manufacturing Microneedle

Similarly to the above Example, the original plate of the microneedle was fabricated by micromachining of a silicon substrate. The silicon substrate was provided with a disc shaped substrate and 36 projections, each formed in a regular quadrangular pyramid shape with a height H of 150 μm and a base side length of 60 μm. The respective 36 projections were disposed with an interval of 1 mm in a matrix of 6 columns and 6 lines.

Then, the original plate of the microneedle formed of a silicon substrate was plated with a nickel to form a nickel film with a thickness of 500 μm. After the nickel film was formed, the original plate was etched by wet etching by using 30 wt % potassium hydroxide aqueous solution heated to 90° C. to form an intaglio plate made of nickel.

After the intaglio plate was fabricated, hydroxypropyl cellulose in the liquid form was supplied to the intaglio plate. Then, hydroxypropyl cellulose was cured by heat from a heat source. The cured hydroxypropyl cellulose was peeled off from the intaglio plate to obtain the microneedle having the substrate 21 and the plurality of projections 22. The obtained microneedle was the same as the microneedle of Example.

Step of Manufacturing Support Section

In manufacturing of the support section, two urethane sheets were provided as the base layer. The two urethane sheets were the same as Example and had the disc shape with the same size.

Then, an acrylic acid adhesive was applied on both surfaces of one of the urethane sheet, and the two urethane sheets were bonded together by adhering one surface of one of the urethane sheets to a surface on which the acrylic acid adhesive was applied. Thus, the support section which included an adhesive layer on one surface was provided.

Step of Manufacturing Microneedle Unit

The supported surface 21b of the microneedle was bonded to the adhesive layer that constituted the bonding surface of the support section of the Comparison example to thereby form the microneedle unit.

As already described above, the manufactured microneedle of the Comparison example is the same as the microneedle unit of Example except for not having the polyester plate member (rigid plate 42).

Evaluation

The manufactured microneedle unit of Example and the microneedle unit of Comparison example were evaluated in the following method.

(1) While stretching the skin, the microneedle of the microneedle unit was pressed against the skin to attach the adhesive layer to the skin.

(2) The microneedle unit was left attached for 2 hours.

(3) The microneedle unit was peeled off from the skin, and the projections on the surface of the microneedle were observed by using a stereoscopic microscope.

The observation result showed that the projections were dissolved in the microneedle of Example. On the other hand, parts of the projections were not dissolved in the microneedle of Comparison example, compared with the microneedle of Example. It seems that, in the microneedle unit of the Comparison example, some of the projections of the microneedle were detached from the skin after they were pierced into the skin, and were not sufficiently dissolved by water in the skin.

As described above, it was confirmed that the microneedle unit of Example having the rigid section can prevent detachment of the projections of the microneedle after pierced into the skin.

As described above, according to the microneedle unit of the present embodiment, the effects listed below can be achieved.

(1) When the microneedle 11 is pierced into the skin, a portion of the skin surface against which the microneedle unit 10 is pressed is stretched by a user so that the microneedle unit 10 is pressed against the stretched skin surface. When the microneedle 11 is pierced into the skin, the adhesive layer 31 is adhered to the skin surface. Accordingly, in the support section 12 of the microneedle unit 10, a restoring force of the skin is applied from the skin surface to the adhesive layer 31 adhered to the skin surface while the rigidity of the rigid plate 42 acts on the adhesive layer 31 via the rigid section 42 bonded to the adhesive layer 31 so as to reduce deformation of the adhesive layer 31. As a result, contraction of the skin is reduced or the speed of shrinkage of the skin is lowered, thereby preventing the microneedle 11 from being easily detached from the skin.

(2) The rigid plate 42 extends in the first direction D1. Accordingly, when the rigid plate 42 and the stretched direction of the skin are parallel, the support section 12 has a maximum effect of preventing deformation of the skin. On the other hand, when the extending direction of the rigid plate 42 intersects the stretched direction of the skin, the support section 12 also prevents deformation of the skin to a certain extent.

(3) When the microneedle 11 is pierced into the skin, the rigid plate 42 is deformed so that the projection forming surface 21a conforms to the skin surface, and the adhesive layer 31 is adhered to the skin surface with the rigid plate 42 deformed. Since the rigid plate 42 has a shape extending along the skin surface while the microneedle 11 is pierced into the skin, the microneedle 11 is not easily detached from the skin compared with the case where the adhesive layer 31 is adhered to the skin surface while the rigid plate does not extend along the skin surface.

(4) When the forming material of the rigid plate 42 is a resin, the rigid plate 42 has the rigidity suitable for use on the human skin, in particular, the skin of the face or arm. Accordingly, the rigid plate 42 can prevent detachment of the microneedle 11 from the skin by suppressing deformation of the skin, and reduce a feeling of tightness of the skin on the puncture target of the microneedle 11 by suppressing deformation of the skin.

(5) Since the surface of the support section 12 opposite from the bonding surface 12a is a pale orange tone, the difference between the color of skin and the color of the microneedle unit 10 placed on the skin can be reduced when the punctuation target of the microneedle 11 is a human. Accordingly, the contrast between the microneedle unit 10 and the skin can be reduced.

(6) In the support section 12, the contrast between the microneedle unit 10 and the skin can be reduced since the reflection of light is reduced on the mat finish surface.

The above embodiment may be appropriately modified as below. In FIGS. 8 to 14, for convenience of explanation of a shape of the rigid plate, the cover layer of the base layer is not shown.

In the support section 12, a surface of the cover layer 41b opposite from the bonding surface 12a may not necessarily have a mat finish.

In the support section 12, a surface of the cover layer 41b opposite from the bonding surface 12a may not necessarily be a pale orange color. The surface opposite from the bonding surface 12a may be in any color such as white, or the support section 12 may be transparent.

As described above, the forming material of the rigid plate 42 may not be limited to a resin, but may also be a material such as a metal. In other words, the forming material of the rigid plate 42 may be any material as long as the rigid plate 42 bends when an external force is applied on the rigid section 32 and the rigid plate 42 has rigidity higher than rigidity of the adhesive layer 31 and the microneedle 11.

Figure 8:
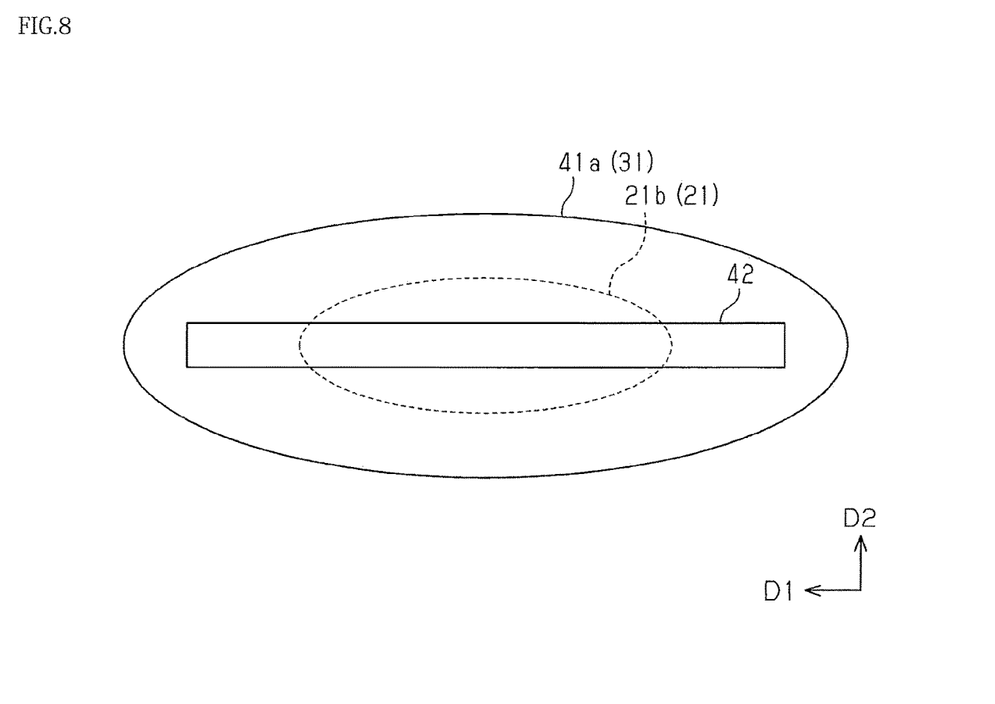
FIG. 8 is a plan view which shows a plan configuration of a rigid plate according to a modified example.

As shown in FIG. 8, the adhesive layer 31 and the base layer 41 may have an oval plate shape extending in the first direction D1, and the rigid plate 42 may have a plate shape extending in the first direction D1. In this configuration, the width of the base layer 41 in the first direction D1 is larger than the width of the base layer 41 in the second direction D2. The user of the microneedle unit 10 can pierce the microneedle 11 into the skin while aligning the extending direction of the rigid plate 42 and the stretching direction of the skin. Accordingly, the rigidity of the rigid plate 42 can serve as a force that suppresses deformation of the skin. The substrate 21 of the microneedle 11 may have a disc shape as described above or may have, for example, an oval disc shape corresponding to the shape of the adhesive layer 31.

Figure 9:
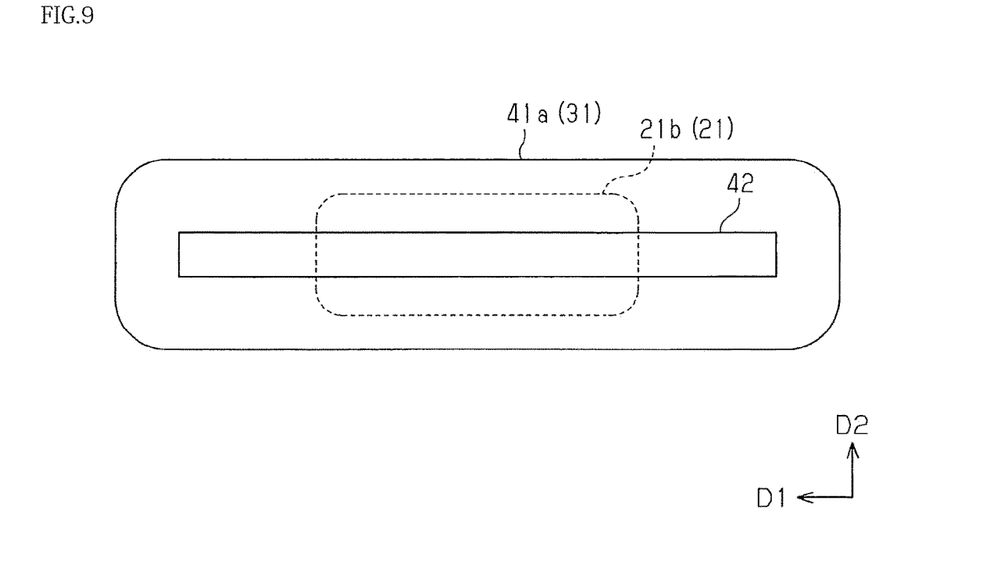
FIG. 9 is a plan view which shows a plan configuration of a rigid plate according to a modified example.

As shown in FIG. 9, the adhesive layer 31 and the base layer 41 may have rectangular plate shape extending in the first direction D1, and the rigid plate 42 may have a plate shape extending in the first direction D1. In this configuration, the width of the base layer 41 in the first direction D1 is larger than the width of the base layer 41 in the second direction D2. The user of the microneedle unit 10 can pierce the microneedle 11 into the skin while aligning the extending direction of the rigid plate 42 and the stretching direction of the skin. Accordingly, the rigidity of the rigid plate 42 can serve as a force that suppresses deformation of the skin. The substrate 21 of the microneedle 11 may have a disc shape as described above or may have, for example, a rectangular plate shape corresponding to the shape of the adhesive layer 31.

Figure 10:
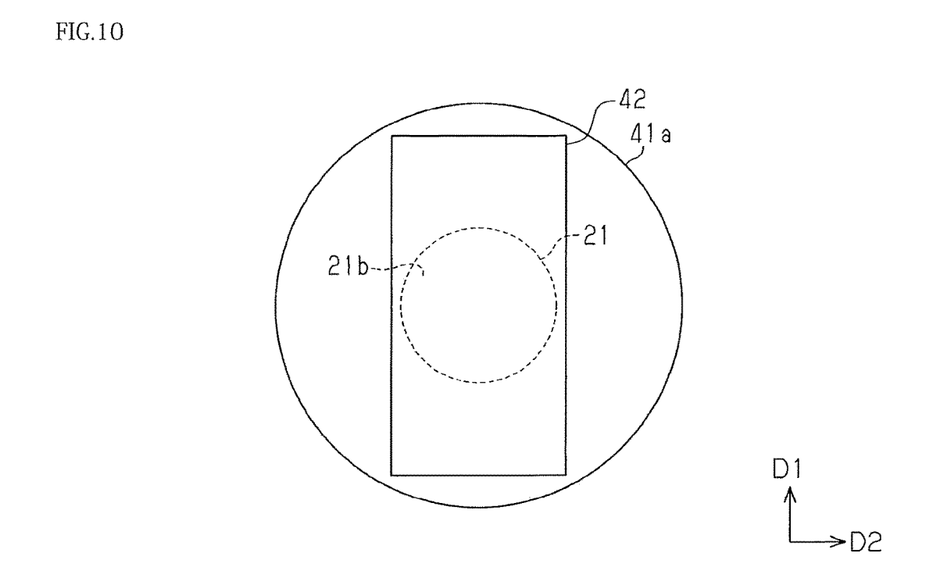
FIG. 10 is a plan view which shows a plan configuration of a rigid plate according to a modified example.

As shown in FIG. 10, the width of the rigid plate 42 in the second direction D2 may be larger than the diameter of the microneedle 11, and the rigid plate 42 may extend beyond the microneedle 11 in plan view of the supported surface 21b of the microneedle 11. In this configuration, when the extending direction of the rigid plate 42 intersects the stretched direction of the skin, the rigidity of a portion of the rigid plate 42 which extends beyond the microneedle 11 can suppress deformation of the skin. As a result, the entire area of the portion of the skin which is in contact with the microneedle 11 is prevented from being deformed, thereby further preventing detachment of the microneedle 11 from the skin.

In the rigid plate 42, the width in the first direction D1 may be the same as the width in the second direction D2.

Figure 11:
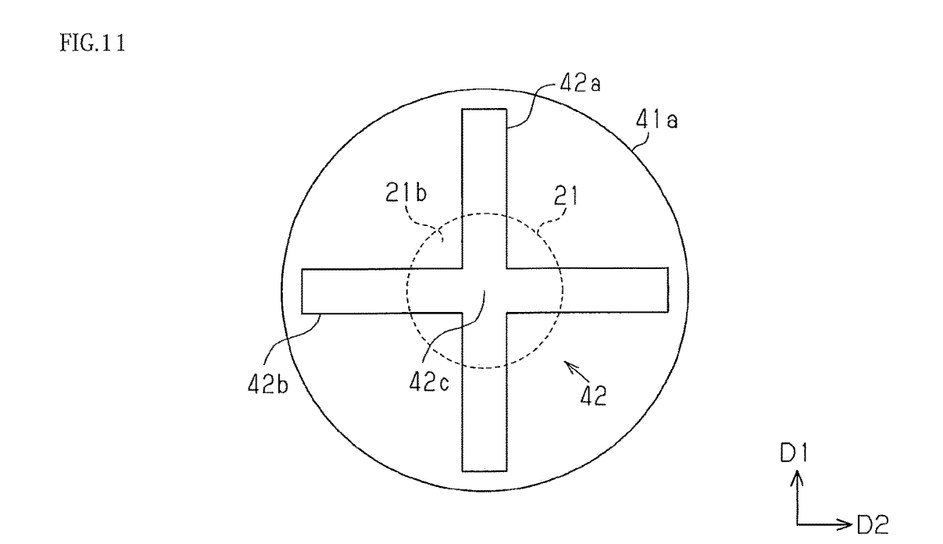
FIG. 11 is a plan view which shows a plan configuration of a rigid plate according to a modified example.

As shown in FIG. 11, the rigid plate 42 may include a first plate portion 42a extending in the first direction D1 and a second plate portion 42b extending in the second direction D2. According to this configuration, the following effects can be obtained.

(7) Both the extending direction of the first plate portion 42a and the extending direction of the second plate portion 42b intersect the stretched direction of the skin stretched by a user even if the stretched direction of the skin does not correspond to the extending direction of the rigid section 32. Accordingly, when the skin deforms in the contracting direction, both the first plate portion 42a and the second plate portion 42b apply a reaction force that suppresses deformation of the skin to a certain extent. As a result, an effect of preventing deformation of the skin by the adhesive layer 31 and the rigid plate 42 can be easily achieved regardless of the relation between the stretched direction of the skin and the extending direction of the rigid plate 42.

Further, in plan view of the supported surface 21b of the microneedle 11, an intersection region 42c of the first plate portion 42a and the second plate portion 42b in the rigid plate 42 may partially overlap the microneedle 11. According to this configuration, the following effects can be obtained.

(8) The first plate portion 42a and the second plate portion 42b of the rigid plate 42 each extend radially from the microneedle 11 in plan view of the supported surface 21b. The microneedle 11 is typically located at the center of a portion of the skin stretched by a user. Accordingly, the first plate portion 42a and the second plate portion 42b of the rigid plate 42 extend radially from the center of the portion of the skin stretched by the user. As a result, an effect of preventing deformation of the skin by the rigid plate 42 can be easily applied on the entire portion of the skin stretched by the user.

Figure 12:
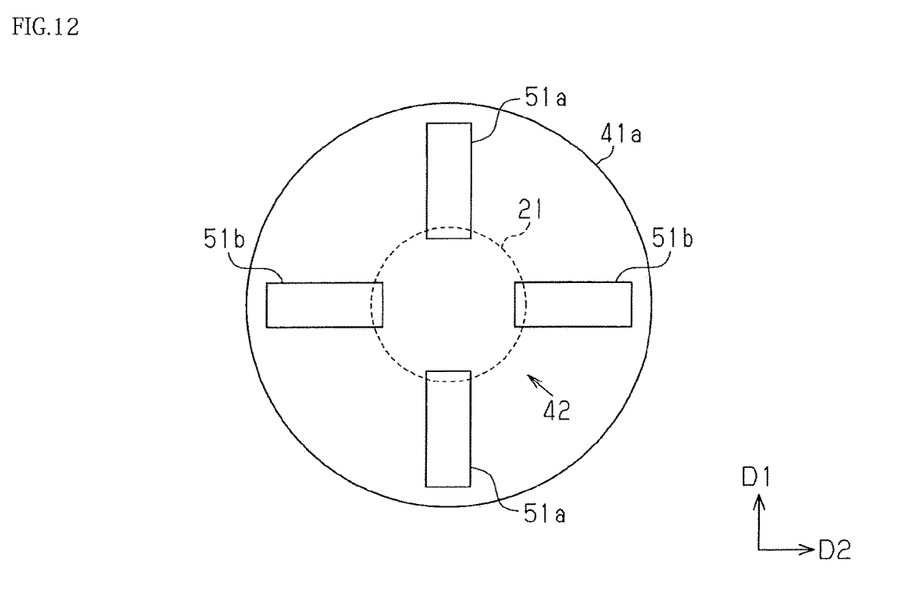
FIG. 12 is a plan view which shows a plan configuration of a rigid plate according to a modified example.

As shown in FIG. 12, the rigid plate 42 may include two first plate portions 51a extending in the first direction D1 and two second plate portions 51b extending in the second direction D2. In this configuration, the two first plate portions 51a may be located on the same straight line parallel to the first direction D1 and the two second plate portions 51b may be located on the same straight line parallel to the second direction D2, and the two first plate portions 51a and the two second plate portions 51b may be radially arranged about the substrate 21 of the microneedle 11. The rigid plate 42 may also be disposed at a position which does not overlap the microneedle 11 in plan view of the supported surface 21b.

Figure 13:
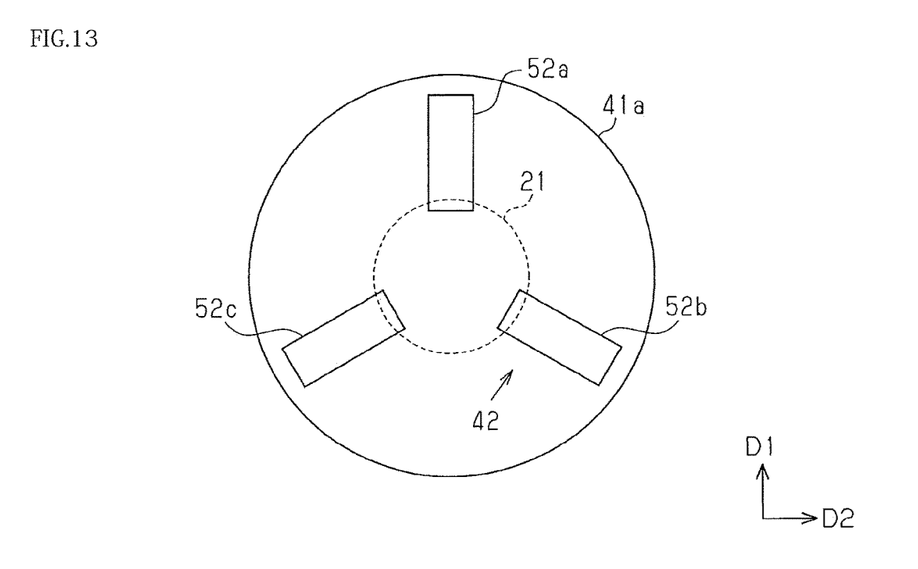
FIG. 13 is a plan view which shows a plan configuration of a rigid plate according to a modified example.

As shown in FIG. 13, the rigid plate 42 may include the first plate portion 52a, the second plate portion 52b and a third plate portion 52c so that the first plate portion 52a, the second plate portion 52b, and the third plate portion 52c are radially arranged about the substrate 21. The rigid plate 42 may also be disposed at a position which does not overlap the microneedle 11 in plan view of the supported surface 21b.

The rigid section 32 may also include a plurality of rigid plates. That is, as shown in FIG. 14, a plurality of rigid plates 53 may be arranged, for example, in the second direction D2 with a predetermined interval with each rigid plates 53 extending in the first direction D1.

Figure 14:
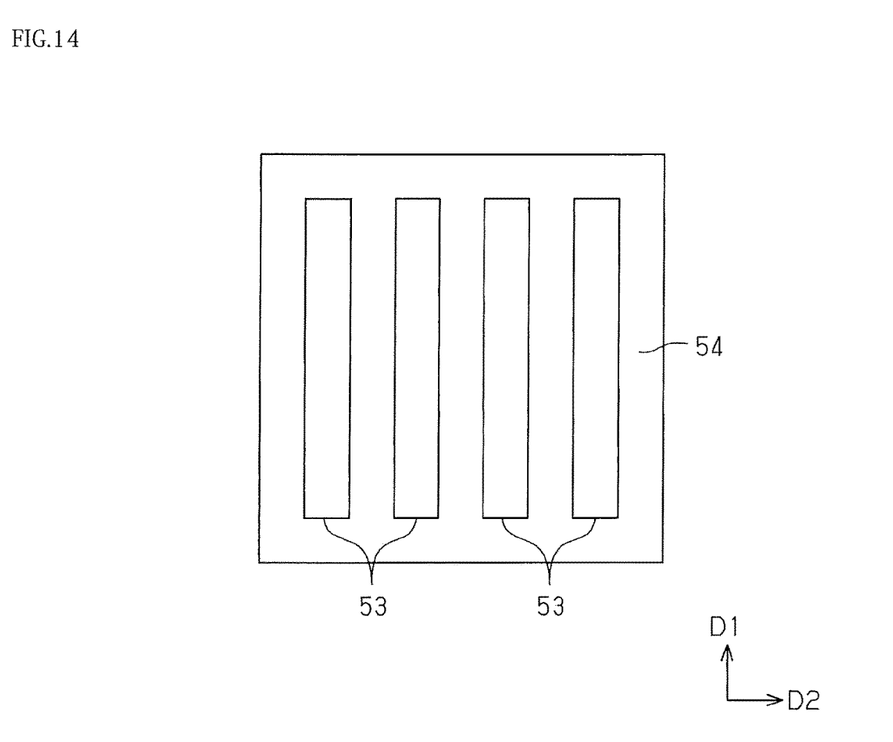
FIG. 14 is a plan view which shows a plan configuration of a rigid plate according to a modified example.

As shown in FIG. 14, the support layer 54 of the support section 12 may have a rectangular plate shape extending in the first direction D1 and the second direction D2. In this configuration, when the rigid section 32 includes a plurality of rigid plates 53 extending in the first direction D1, an effect of preventing deformation of the skin by the rigid plate 42 can be easily achieved regardless of the stretched direction of the skin as described above.

Since the rigid section 32 is made up of the base layer 41 and the rigid plate 42, the rigidity of the base layer 41 may be the same as the rigidity of the rigid plate 42. In this configuration, an effect similar to that of the (1) can also be achieved as far as the rigidity of the rigid section 32 is higher than the rigidity of the adhesive layer 31 and the microneedle 11. In the rigid section 32, the rigidity of the base layer 41 is preferably lower than the rigidity of the rigid plate 42 considering improvement in the conformability to the skin surface. Further, as far as the rigidity higher than that of the microneedle 11 and the rigidity higher than that of the adhesive layer 31 are assured by the rigid plate 42 that constitutes the rigid section 32, the rigidity of the base layer 41 may be equal to or lower than the rigidity of the microneedle 11 and the rigidity of the adhesive layer 31.

The rigid section 32 may include only the cover layer 41b, not both the rigid plate 42 and the base layer 41, and the rigid plate 42 may be directly bonded to the adhesive layer 31. In this configuration, an effect similar to that of the above (1) can be obtained.

The rigid section 32 may at least include the rigid plate 42, and may not necessarily include the base layer 41. That is, the rigid plate 42 may be directly bonded to the adhesive layer 31. In this configuration, an effect similar to that of the above (1) can also be achieved as far as the support section 12 has the adhesiveness of the adhesive layer 31 and the rigidity of the rigid plate 42.

The adhesive layer 31 may not be necessarily a portion having adhesiveness, but may be an adhesive section having adhesive properties. In this configuration, an effect similar to that of the above (1) can also be achieved.

The rigid section 42 may not necessarily have flexibility to bend along with the projection forming surface 21a when subject to an external force that bends the projection forming surface 21a of the microneedle 11. That is, the rigid plate 42 may have rigidity of such an extent that does not flex along with the projection forming surface 21a even if the projection forming surface 21a of the microneedle 11 is bent. In this configuration, it is sufficient as long as the adhesive layer 31 has an adhesiveness that ensures adhesion of the adhesive layer 31 and the microneedle 11 to the skin surface when the projection forming surface 21a of the microneedle 11 is bent by an external force and the rigid plate 42 does not flex. Accordingly, an effect similar to the above (1) can be obtained.

Further, if the entire rigid section 32 has a rigidity higher than the rigidity of the microneedle 11 and the adhesive layer 31, the rigid section 32 may not necessarily have flexibility. Even in this configuration, it is sufficient as long as the adhesive layer 31 has an adhesiveness that ensures adhesion of the adhesive layer 31 and the microneedle 11 to the skin surface. Accordingly, an effect similar to the above (1) can be obtained.

The aforementioned embodiment of the microneedle unit 10 and a plurality of modified examples can be implemented in various combinations thereof.

When the microneedle is pierced into the skin, the skin surface is first stretched over the bone of the body by a user, and then the microneedle is pressed against the stretched skin surface. Since the skin surface has elasticity and returns to its original shape from the stretched state, the stretched skin surface contracts to return to the original shape when a force that presses the microneedle against the skin surface is released. Depending on the degree of puncture of the microneedle into the skin or the degree of movement of the skin, the microneedle may be pushed out of the skin as the skin surface contracts, which results in the microneedle detaching from the skin. Accordingly, there is a need for microneedles which are not easily detached from the skin after being pierced into the skin when the user releases a force pressing the microneedle against the skin.

An aspect of the present invention is to provide a microneedle unit that prevents a microneedle pierced into the skin from being detached from the skin.

According to one embodiment, a microneedle unit includes: a microneedle which includes a first surface having at least one projection and a second surface located opposite the first surface, the microneedle having flexibility; and a support section that is bonded to the second surface of the microneedle to supports the microneedle. The support section includes: an adhesive section which extends outside from the second surface in plan view of the second surface, and has adhesiveness to adhere to a skin; and a rigid section bonded to the adhesive section, the rigid section including a rigid plate having a rigidity higher than the rigidity of the adhesive section and higher than the rigidity of the microneedle.

When the microneedle is pierced into the skin, a portion of the skin against which the microneedle unit is pressed is stretched by a user. Then, the microneedle unit is pressed against the stretched skin surface. According to one embodiment of the microneedle unit, when the microneedle is pierced into the skin, the adhesive section is adhered to the skin surface. Further, in the support section of the microneedle unit, a restoring force of the skin is applied from the skin surface to the adhesive section adhered to the skin surface. Meanwhile, rigidity of the rigid section acts on the adhesive section via the rigid section bonded to the adhesive section so as to reduce deformation of the adhesive section. As a result, contraction of the skin is reduced or the speed of contraction of the skin is lowered, thereby preventing the microneedle from being easily detached from the skin.

According to another embodiment of the microneedle unit, it is preferable that the adhesive section extends outside from the rigid plate in plan view of the second surface, and the rigid plate has a plate shape that extends in a first direction.

According to another embodiment of the microneedle unit, the rigid plate extends in the first direction. Accordingly, when the extending direction of the rigid plate and the stretched direction of the skin are parallel, the support section has a maximum effect of preventing deformation of the skin. Further, when the extending direction of the rigid plate intersects the stretched direction of the skin, the support section also prevents deformation of the skin to a certain extent.

According to another embodiment of the microneedle unit, it is preferable that the rigid plate overlaps at least part of the microneedle in plan view of the second surface.

According to another embodiment of the microneedle unit, it is preferable that the rigid section has flexibility to bend along with the first surface when subject to an external force that bends the first surface of the microneedle.

According to another embodiment of the microneedle unit, when the microneedle is pierced into the skin, the rigid section is also deformed so that the first surface conforms to the skin surface, and the adhesive section is adhered to the skin surface with the rigid section deformed. Since the rigid section has a shape extending along the skin surface while the microneedle is pierced into the skin, the microneedle is not easily detached from the skin compared with the case where the adhesive section is adhered to the skin surface while the rigid section does not extend along the skin surface.

According to another embodiment of the microneedle unit, it is preferable that the adhesive section has a plate shape which extends in the first direction and a second direction which intersects the first direction, and the rigid plate further includes a first plate portion having a plate shape which extends in the first direction, and a second plate portion having a plate shape which extends in the second direction.

According to another embodiment of the microneedle unit, since the rigid plate includes the first plate portion and the second plate portion, both the extending direction of the first plate portion and the extending direction of the second plate portion intersect the stretched direction of the skin stretched by the user even if the stretched direction of the skin does not correspond to the extending direction of the rigid plate. Accordingly, when the skin deforms in the contracting direction, a reaction force against deformation of the skin to a certain extent is applied to the skin on the basis of the rigidity of both the first plate portion and the second plate portion. As a result, an effect of preventing deformation of the skin by the rigid plate can be easily achieved regardless of the relation between the stretched direction of the skin and the extending direction of the rigid plate.

According to another embodiment of the microneedle unit, it is preferable that the rigid plate includes an intersection region in which the first plate portion and the second plate portion intersect, and at least a portion of the second surface overlaps the intersection region in plan view of the second surface.

According to another embodiment of the microneedle unit, each of the first plate portion and the second plate portion in the rigid plate radially extend from the microneedle in plan view of the second surface. The microneedle is typically located at the center of a portion of the skin stretched by the user. Therefore, the first plate portion and the second plate portion of the rigid section radially extend from the center of the portion of the skin stretched by the user. As a result, an effect of preventing deformation of the skin by the rigid section can be easily applied on the entire portion of the skin stretched by the user.

According to another embodiment of the microneedle unit, it is preferable that the forming material of the rigid section is a resin.

According to another embodiment of the microneedle unit, the support section has the rigidity suitable for use on human skin, in particular, the skin of the face or arm since the forming material of the rigid section is a resin. Therefore, detachment of the microneedle from the skin can be prevented by suppressing deformation of the skin, and a feeling of tightness of the skin on the puncture target of the microneedle can be reduced by suppressing deformation of the skin.

According to another embodiment of the microneedle unit, it is preferable that a surface of the support section on an opposite side from a surface which is in contact with the second surface has a pale orange tone.

According to another embodiment of the microneedle unit, the difference between the color of skin and the color of the microneedle unit placed on the skin can be reduced when the punctuation target of the microneedle is a human since the surface on an opposite side from the second surface is a pale orange tone. Accordingly, the contrast between the microneedle unit and the skin can be reduced.

According to another embodiment of the microneedle unit, it is preferable that a surface of the support section on an opposite side from a surface which is in contact with the second surface has a mat finish surface.

According to another embodiment of the microneedle unit, the contrast between the microneedle unit and the skin can be reduced since the reflection of light is reduced on the mat finish surface.

According to the microneedle unit of the present invention, the microneedle is prevented from detaching from the skin.

REFERENCE SIGNS LIST

10 . . . microneedle unit, 11 . . . microneedle, 12 . . . support section, 12a . . . bonding surface, 21 . . . substrate, 21a . . . projection forming surface, 21b . . . supported surface, 22 . . . projection, 31 . . . adhesive layer, 32 . . . rigid section, 41 . . . base layer, 41a, 54 . . . support layer, 41b . . . cover layer, 42, 53 . . . rigid plate, 42a,51a, 52a . . . first plate portion, 42b, 51b, 52b . . . second plate portion, 42c . . . intersection region, 52c . . . third plate portion Obviously, numerous modifications and variations of the present invention are possible in light of the above teachings. It is therefore to be understood that within the scope of the appended claims, the invention may be practiced otherwise than as specifically described herein.

What is claimed is:

1. A microneedle unit, comprising:
a flexible microneedle having at least one projection on a first surface; and
a support member connected to a second surface of the flexible microneedle on an opposite side with respect to the first surface of the flexible microneedle such that the support member supports the flexible microneedle,
wherein the support member includes an adhesive layer, a base layer and a rigid plate formed such that the adhesive layer is positioned to adhere to skin and extends outside of the second surface of the flexible microneedle and that the base layer includes a support layer and a cover layer and has a rigidity lower than a rigidity of the rigid plate, and that the rigid plate overlaps with at least a portion of the flexible microneedle, is sandwiched between the support layer and the cover layer in the base layer, and has rigidity that is higher than a rigidity of the adhesive layer and the flexible microneedle.

2. The microneedle unit of claim 1, wherein the adhesive layer extends outside of the rigid plate, and the rigid plate has a plate shape that extends in a first direction.

3. The microneedle unit of claim 2, wherein the rigid plate overlaps with a portion of the flexible microneedle such that the rigid plate has a center part overlapping with a center part of the flexible microneedle.

4. The microneedle unit of claim 3, wherein the base layer and the rigid plate form a rigid portion such that the rigid portion has flexibility to bend along with the first surface of the flexible microneedle when an external force is applied to bend the first surface of the flexible microneedle.

5. The microneedle unit of claim 3, wherein the rigid plate comprises a resin.

6. The microneedle unit of claim 3, wherein the support member has a surface on an opposite side of the second surface of the flexible microneedle such that the surface has a pale orange tone.

7. The microneedle unit of claim 3, wherein the rigid plate overlaps with at least a portion of the at least one projection of the flexible microneedle.

8. The microneedle unit of claim 2, wherein the base layer and the rigid plate form a rigid portion such that the rigid portion has flexibility to bend along with the first surface of the flexible microneedle when an external force is applied to bend the first surface of the flexible microneedle.

9. The microneedle unit of claim 2, wherein the adhesive layer has a plate shape which extends in the first direction and a second direction that intersects the first direction, and the rigid plate includes a first plate-shape portion extending in the first direction, and a second plate-shape portion extending in the second direction.

10. The microneedle unit of claim 9, wherein the rigid plate has an intersection region where the first plate-shape portion intersects with the second plate-shape portion, and at least a portion of the second surface overlaps with the intersection region.

11. The microneedle unit of claim 10, wherein the rigid plate comprises a resin.

12. The microneedle unit of claim 9, wherein the rigid plate comprises a resin.

13. The microneedle unit of claim 2, wherein the rigid plate comprises a resin.

14. The microneedle unit of claim 2, wherein the support member has a surface on an opposite side of the second surface of the flexible microneedle such that the surface has a pale orange tone.

15. The microneedle unit of claim 2, wherein the rigid plate has a first width larger than a diameter of the flexible microneedle in the first direction, and a second width smaller than the diameter of the flexible microneedle in the second direction.

16. The microneedle unit of claim 1, wherein the rigid plate overlaps with a portion of the flexible microneedle such that the rigid plate has a center part overlapping with a center part of the flexible microneedle.

17. The microneedle unit of claim 1, wherein the base layer and the rigid plate form a rigid portion such that the rigid portion has flexibility to bend along with the first surface of the flexible microneedle when an external force is applied to bend the first surface of the flexible microneedle.

18. The microneedle unit of claim 1, wherein the rigid plate comprises a resin.

19. The microneedle unit of claim 1, wherein the support member has a surface on an opposite side of the second surface of the flexible microneedle such that the surface has a pale orange tone.

20. The microneedle unit of claim 1 wherein the support member has a surface on an opposite side of the second surface of the flexible microneedle such that the surface has a matte finish surface.

* * * * *